United States Patent [19]

de Ruggieri et al.

[11] 4,052,352

[45] Oct. 4, 1977

[54] TETRAHYDROPYRANYL ETHERS OF ESTROGENS

[75] Inventors: Pietro de Ruggieri; Orazio Sighinolfi, both of Milan, Italy

[73] Assignee: Farmilla Farmaceutici Milano S.p.A., Italy

[21] Appl. No.: 633,474

[22] Filed: Nov. 19, 1975

[30] Foreign Application Priority Data

Dec. 13, 1974 Italy .................................. 30574/74

[51] Int. Cl.$^2$ ............................................. C07J 17/00
[52] U.S. Cl. ......................... 260/239.55 R; 260/397.5
[58] Field of Search ......... 260/397.5, 239.55, 397.5 A

[56] References Cited

U.S. PATENT DOCUMENTS 2,208,915  7/1940  Weisz ............................... 260/397.5

3,481,924  12/1969  De Ruggeri et al. ........... 260/239.55

FOREIGN PATENT DOCUMENTS 911,600  11/1962  United Kingdom .............. 260/397.5

OTHER PUBLICATIONS

"Steroids", by Fieser et al. (1959), pp. 452, 455, 459 relied on.

*Primary Examiner*—Elbert L. Roberts
*Attorney, Agent, or Firm*—Hill, Gross, Simpson, Van Santen, Steadman, Chiara & Simpson

[57] ABSTRACT

Tetrahydropyranyl ethers of estrogens have interesting properties in the cure of climateric and menopausal disturbances, with an excellent dissociation index between their selective effect on the vagina and their very small or zero effect on the endometrium.

5 Claims, No Drawings

TETRAHYDROPYRANYL ETHERS OF ESTROGENS

THIS INVENTION provides, as new compounds, the estrogen derivatives of the formula:

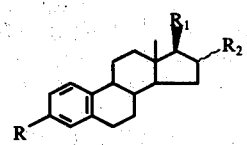

where R is 2'-tetrahydropyranyloxy or benzyloxy, $R_1$ is β-hydroxy, β-acyloxy of 2 to 10 carbon atoms, e.g. β-acetoxy, $R_2$ is β-hydroxy, or β-acyloxy of 2 to 10 carbon atoms with the proviso that, when $R_1$ = β-hydroxy and $R_2$ = β-hydroxy, R is 2-tetrahydropyranyloxy.

It should be noted that the introduction of the tetrahydropyranyloxy radical comprising one asymmetrical carbon atom leads to two diastereoisomers R and S with a possible α and β anomer configuration, the α (axial) configuration being the preferred, as it is stabilized by two ethereal dipoles of antiparallel position on the two oxygen atoms present.

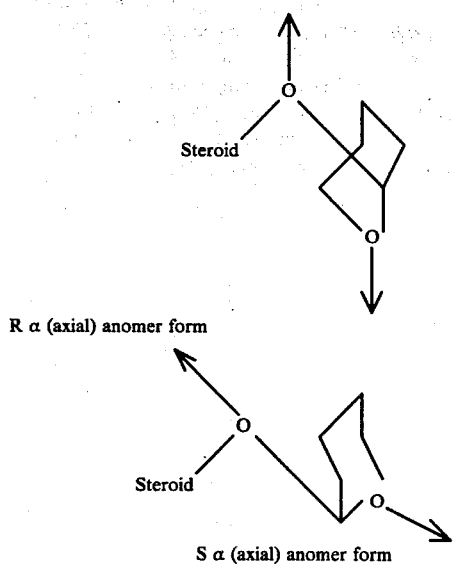

The present invention therefore relates both to the mixture R + S and to the two separate R and S diastereoisomers.

These compounds, derived from the estrogen series, have favourable therapeutic properties in the cure of climateric and menopausal disturbances, with an excellent dissociation index between their selective effect on the vagina and their very small or zero effect on the endometrium; the administration of the compounds can be effected orally, in the form of capsule, tablets, dragees or by injection in oil solution, with daily dosages from 1 to 25 mg. for treatments continued for 3 weeks, followed by an interruption of one week, or for more extended cycles.

The compounds with free $C_{16}$ and $C_{17}$ hydroxy groups are prepared as in Equation 1, by reducing (I) (which is described by M. N. Huffman and M. H. Lott, J. Biol, Chem. 172, 325 (1948)) with complex hydrides or Na/alcohol: in the first case the cis-diol (II a), in the second the trans-diol (II b) are obtained.

Equation I

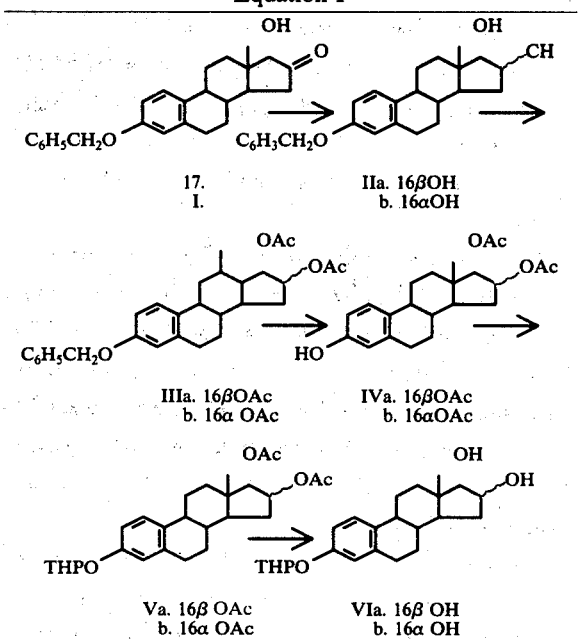

In particular the 3-benzyloxy-estra-1,3,5(10)-trien-16β,17β-diol (IIa), after protecting the alcoholic groups as the acetates, restoring the phenolic function by destructive hydrogenation (i.e., hydrogenolysis of the benzyl group in an organic solvent) and etherifying the phenolic function with 2,3-dihydropyran, in the presence of an acid catalyst selected from the group consisting of p-toluene sulphonic acid, $POCl_3$, or HCl gave 3-(2'-tetrahydropyranyloxy)-estra-1,3,5-(10)-triene-16β,17β-diacetate (V a), which after hydrolysis of the acetate groups, finally gave 3-(2'-tetrahydropyranyloxy)-estra-1,3,5(10)-triene-16β,17β-diol (VI a).

The 3-(2'-tetrahydropyranyloxy)-estra-1,3,5(10)-trien-16α,17β-diol isomer (VI b) was obtained analogously starting from the trans-diol (II b).

The following Examples illustrate the present invention.

EXAMPLE 1

3-(2'-Tetrahydropyranyloxy)-estra-1,3,5(10)-trien-16β,17β-diol (VI a).

A solution of 10 parts of 3-benzyloxy-estra-1,3,5(10)-trien-16β,17β-diol (II a) in 40 parts of pyridine and 10 parts of acetic anhydride is left to stand overnight. When the reaction mixture is added to ice-cold water, a precipitate is formed which is filtered off, dried and crystallized from methanol to give 8.5 parts of 3-benzyloxy-16β,17β-diacetoxy-estra-1,3,5(10)-triene (III a), m.p. 105°-7° C. and $[α]_D = +58.5°$ (chloroform).

The product thus obtained is dissolved in 250 parts of dioxano and 400 parts of ethanol and hydrogenated in the presence of 8,5 part of carbon containing 5% of palladium, to give 6.5 parts of 16β,17β-diacetoxy-estra-1,3,5(10)-trien-3-ol (IV a) m.p. 222°-5° C. and $[α]_D = +69°$ (chloroform), which is used directly for the next step. A solution of 2,5 parts of (IV a) in 40 parts of tetrahydrofuran mixed with 90 parts of anhydrous benzene is added to a solution of 5 parts of 2,3-dihydropyran in 180 parts of anhydrous benzene containing 0,15 parts of p-toluenesulphonic acid. After leaving overnight at room temperature, it is washed with a 10% NaHCO₃ solution and then with water until neutral. The organic phase is dried and then concentrated to dryness under vacuum. Direct crystallisation from ethyl ether-hexane gives 6,8 parts of 3-(2'-tetrahydropyranyloxy)-16β,17β-diacetoxy-estra-1,3,5(10)-triene (V a), m.p. 128–30° C. and [α]$_D$ = + 40° (chloroform).

The protecting groups are hydrolysed by dissolving the product (V a) in 600 parts of 5% KOH in methanol in an oxygen-free atmosphere and boiling under reflux for one hour thirty minutes. The crude product is isolated and then crystallised from ethyl ether-hexane to give 5 parts of 3-(2'-tetrahydropyranyloxy)-estra-1,3,5(10)-trien-16β,17β-diol (VI a), m.p. 106°–8° C. and [α]$_D$ = + 59° (chloroform).

As stated above this compound is the mixture of the two diastereoisomers R and S. By fractional cristallization from methanol, the mixture gives the pure forms: 3-(2'-R-tetrahydropyranyloxy)-estra-1,3,5(10)-trien-16β,17β-diol, m.p. 124°–5° C, [α]$_D$ = + 92° (CHCl₃), and 3-(2'-S-tetrahydropyranyloxy)-estra-1,3,5(10)-trien-16β,17β-diol, m.p. 102°–6° C and [α]$_D$ = + 30 (CHCl₃).

What we claim is:

1. Compounds of the formula:

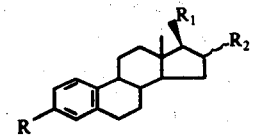

where R is 2'-tetrahydropyranyloxy; R₁ is beta-hydroxy; R₂ is beta-hydroxy with the proviso that, when R₁ and R₂ are beta-hydroxy, R is 2'-tetrahydropyranyloxy.

2. A process for preparing 3-(2'-tetrahydropyranyloxy)-estra-1,3,5(10) — trien-16 beta, 17 beta — diol which comprises reacting a corresponding 3-benzyloxy — 16 beta, 17 beta-dihydroxy compound with an acetic anhydride or an acetyl chloride, subjecting the 16, 17-diester so-obtained to hydrogenolysis of the benzyl group in an organic solvent, etherifying the phenolic function thus liberated with 2,3-dihydropyran in the presence of an acid catalyst selected from the group consisting of p-toluenesulphonic acid, POCl₃ and HCl, and finally removing the acetate groups by alkaline hydrolysis.

3. Process according to claim 2 in which the esterification is effected in pyridine, the hydrogenolysis is effected with ethanol alone or mixed with dioxane, tetrahydrofuran or ethyl acetate, in the presence of 2.5 to 10% Pd on carbon, and the etherification is carried out in the presence of p-toluenesulphonic acid, in 2,3-dihydropyran, tetrahydrofuran, dioxane or benzene.

4. A compound comprising of 3-(2'-tetrahydropyranyloxy)-16β,17β-diacetoxyestra-1,3,5(10)-triene.

5. A compound comprising of 3-(2'-tetrahydropyranyloxy)-estra-1,3,5(10)-trien-16β, 17β-diol.

* * * * *

UNITED STATES PATENT OFFICE
CERTIFICATE OF CORRECTION

Patent No. 4,052,352            Dated October 4, 1977

Inventor(s) Pietro de Ruggieri, et al

It is certified that error appears in the above-identified patent and that said Letters Patent are hereby corrected as shown below:

Equation I should read as follows:

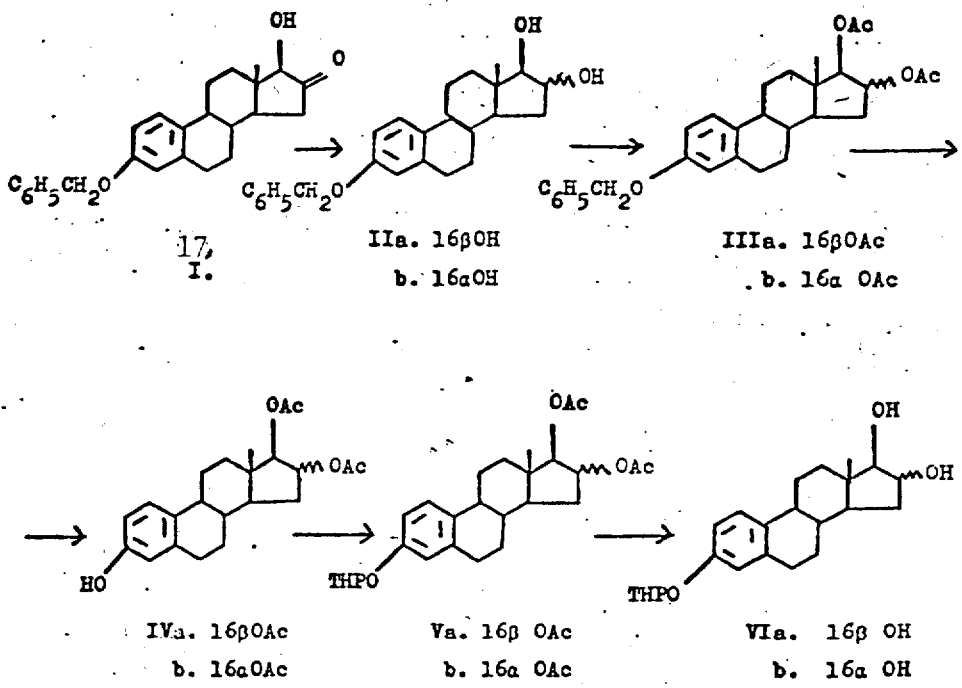

Signed and Sealed this

Thirtieth Day of May 1978

[SEAL]

Attest:

RUTH C. MASON
Attesting Officer

LUTRELLE F. PARKER
Acting Commissioner of Patents and Trademarks